(12) United States Patent
Schiltz et al.

(10) Patent No.: US 10,598,604 B1
(45) Date of Patent: Mar. 24, 2020

(54) NORMAL INCIDENCE PHASE-SHIFTED DEFLECTOMETRY SENSOR, SYSTEM, AND METHOD FOR INSPECTING A SURFACE OF A SPECIMEN

(71) Applicant: Carl Zeiss Industrial Metrology, LLC, Maple Grove, MN (US)

(72) Inventors: Drew Schiltz, Maple Grove, MN (US); Nathaniel Roisen, Minneapolis, MN (US)

(73) Assignee: Cark Zeiss Industrial Metrology, LLC, Maple Grove, MN (US)

( * ) Notice: Subject to any disclaimer, the term of this patent is extended or adjusted under 35 U.S.C. 154(b) by 0 days.

(21) Appl. No.: 16/396,490

(22) Filed: Apr. 26, 2019

(51) Int. Cl.
*G01N 21/88* (2006.01)

(52) U.S. Cl.
CPC ... *G01N 21/8806* (2013.01); *G01N 2201/062* (2013.01)

(58) Field of Classification Search
CPC ..... G03N 21/253; G03N 21/8806; G01N 2/88
USPC .................................................. 356/73, 237.2
See application file for complete search history.

(56) References Cited

U.S. PATENT DOCUMENTS

| | | | |
|---|---|---|---|
| 6,766,046 B1 | 7/2004 | Saito et al. | |
| 2005/0099622 A1* | 5/2005 | Caracci | G01N 21/253 356/300 |
| 2006/0164626 A1* | 7/2006 | Meeks | G01B 11/303 356/73 |
| 2016/0025591 A1 | 1/2016 | Risner et al. | |
| 2017/0041577 A1* | 2/2017 | Nishimura | G02B 23/24 |
| 2017/0132801 A1 | 5/2017 | Trenholm et al. | |
| 2017/0205342 A1* | 7/2017 | Krishnan | G01J 3/18 |
| 2017/0221198 A1 | 8/2017 | Dacquin et al. | |
| 2017/0227471 A1 | 8/2017 | Cilip et al. | |

FOREIGN PATENT DOCUMENTS

DE        102008038256 A1        2/2010

OTHER PUBLICATIONS

Huang, Run, „High Precision Optical Surface Metrology Using Deflectometry, University of Arizona, PhD Thesis, 2015.

* cited by examiner

*Primary Examiner* — Hung Nguyen
(74) *Attorney, Agent, or Firm* — Falk Ewers; Ewers IP Law PLLC

(57) ABSTRACT

A system for inspecting a surface of a specimen includes a normal incidence phase-shifted deflectometry (PSD) sensor including an imaging sensor, a beam splitter, and an imaging optic arranged between the imaging sensor and the beam splitter. The illumination source illuminates the specimen with a light pattern and is arranged perpendicular to the surface of the specimen. The imaging sensor captures the light pattern reflected from the surface of the specimen in a sensor image. The beam splitter directs a first portion of the light from the illumination source to the optical absorber, a second portion of the light from the illumination source to the surface of the specimen, and the light pattern reflected from the surface of the specimen to the imaging sensor. A data processing apparatus in communication with the normal incidence PSD sensor determines properties of the surface of the specimen based on the sensor image.

20 Claims, 9 Drawing Sheets

NORMAL INCIDENCE PHASE-SHIFTED DEFLECTOMETRY SENSOR, SYSTEM, AND METHOD FOR INSPECTING A SURFACE OF A SPECIMEN

TECHNICAL FIELD

The invention relates to a normal incidence phase-shifted deflectometry (PSD) sensor for inspecting a surface of a specimen, a system for inspecting a surface of a specimen with the normal incidence PSD sensor, and a method for inspecting a surface of a specimen with the normal incidence PSD sensor.

BACKGROUND

White light surface inspection systems have been developed for high throughput and highly automated manufacturing of products with decorative and technical surfaces. These systems facilitate a high degree of sensitivity to even the smallest changes in form and gloss level on a myriad of types of surfaces and finishes.

A conventional phase-shifted deflectometry setup 100 is shown in FIG. 1. The setup includes a surface 110 of an object under test, a pattern area 120 generated by an illumination unit (not shown), a camera 130, and an image evaluation unit 140 with a display. The camera 130 sequentially takes a plurality of images of the reflected pattern area, which are subsequently evaluated by the image evaluation unit 140.

The phase-shifted deflectometry setup shown in FIG. 1 requires the illumination unit, the camera, and the surface of the object under test to be in a fixed spatial location to each other while the plurality of images is taken by the camera.

A conventional device for optically inspecting a surface of a sample to determine quality parameters of a product and to identify surface defects based on white light phase-shifted deflectometry is described, e.g., in U.S. Patent Application Publication No. 2017/0227471. The device includes a screen which provides profile patterns with areas that form spatial light intensity profiles and a curved mirror arranged between the screen and a holder for providing a second light profile pattern. Like the setup shown in FIG. 1, the device described in U.S. Patent Application Publication No. 2017/0227471 requires an image recording unit to record a plurality of images to determine properties of the surface of the sample.

The setup shown in FIG. 1 begins to exhibit serious limitations when moving into a softmicroscopy regime; that is defocus blur begins to become a major limitation. In a typical deflectometry setup, such as the setup shown in FIG. 1, the camera has to be held at an angle to the portion of the surface to be inspected to be able to image reflected light coming from the illumination unit. As the object pixel size of the camera is decreased, and thus the useable depth of field also depreciates, the useable field of view begins to shrink significantly. The implications are that for imaging of large areas on a test surface, many more inspection "poses" are required, and thus the overall cycle time for the inspection of the test piece increases significantly.

SUMMARY

It is therefore an object of the present invention to provide a sensor, a system, and a method for inspecting a surface of a specimen which allows surface inspection with a high throughput. In particular, it is an object of the invention to provide a sensor, a system, and a method that allows a high depth sensitivity over a rather large dynamic range combined with a high speed of data acquisition.

The object is achieved by a normal incidence PSD sensor for optically inspecting the surface of a specimen, wherein the normal incidence PSD sensor includes an illumination source configured to illuminate the specimen with a light pattern, the light pattern including first areas in which light is emitted with a first light intensity and second areas in which the light is emitted with a second light intensity, the first light intensity being higher than the second light intensity, the illumination source being arranged relative to the surface of the specimen to permit the illumination source to emit the light perpendicular to the surface of the specimen, an imaging sensor configured to capture the light pattern reflected from the surface of the specimen in a sensor image, an optical absorber or light sink configured to absorb a first portion of the light emitted from the illumination source, a beam splitter arranged between the illumination source and the optical absorber and configured to direct (a) the first portion of the light from the illumination source to the optical absorber, (b) a second portion of the light from the illumination source to the surface of the specimen, and (c) the light pattern reflected from the surface of the specimen to the imaging sensor; and an imaging optic arranged between the imaging sensor and the beam splitter.

The normal incidence PSD sensor technology relies on phase-shifted deflectometry. Similar to the white light sensor technology, the normal incidence technique of phase-shifted deflectometry uses three conditions: (1) the surface of an object to be inspected is at least partially glossy, (2) the specimen is illuminated with a spatial intensity light pattern, and (3) a camera or light sensor captures the spatial light intensity pattern reflected or scattered from the surface of the object to be inspected.

The normal incidence PSD sensor technology allows to inspected surfaces made of glass, such as surfaces of mirrors or of optical lenses, and silicon surfaces. In addition, magnification levels can be increased and the area that the normal incidence PSD sensor is able to scan can be maximized in comparison with the conventional white light surface inspection systems when inspecting planar or near planar surfaces.

In the case of white light sensor technology, three or more acquisitions are taken from the spatial intensity light pattern by the camera. The only difference between each acquisition is the illumination condition. For example, if the spatial light intensity pattern is a sinusoidal light intensity pattern, the sinusoidal pattern shifts by $n*2\Pi/n_{tot}$, where n is the $n^{th}$ acquisition and $n_{tot}$ is the total number of acquisitions in the sequence.

After the three or more acquisitions are taken, post-calculated images can be generated, including images for main grayscale, phase, and amplitude channels. The grayscale channel represents an average light intensity of the three images. The amplitude channel carries information about changes in gloss on the surface. The phase is directly comparable to the slope of the surface of the object. Fully utilizing all of the information from these post-calculated image sets, algorithms are then developed to find irregularities based on scattering qualities of an anomaly or physical changes in depth on the surface. Sensitivity to sub-micron depth on the surface is common-place, making such a system ideal for inspection of defects such as dents, bumps, scratches, waviness, or orange peel to name a few.

However, a main difference between the white light sensor technology and the normal incidence technique technology is the positioning of the normal incidence PSD sensor relative to the surface of the specimen to be inspected. While the white light sensor technology requires the illumination unit and the camera to be separate entities arranged in separate locations and at certain angles relative to the portion of the surface to be inspected to be able to image reflected light coming from the illumination unit, the normal incidence PSD sensor includes both, the illumination source and the imaging sensor. This is achieved by providing a 50/50 beam splitter which is inserted in the light beam path and which allows emitting normal incidence light from the illumination source to the surface and collecting light reflected from the surface of the specimen in an acquisition without changing the position of the normal incidence PSD sensor.

As described above, the illumination source is arranged on a first side of the beam splitter and an optical absorber is arranged on a second side of the beam splitter opposite to the first side. The beam splitter directs a first portion of the light with the light pattern emitted from the illumination source to the optical absorber. A second portion of the light emitted from the illumination source is directed by the beam splitter to the surface of the specimen, and the light pattern reflected from the surface of the specimen is directed by the beam splitter to the imaging sensor. The optical absorber may be an antireflective neutral density (AR ND) filter which is placed opposite to the illumination source to quell any light carrying any information that may pollute the light pattern reflected from the surface of the specimen.

According to an aspect of the invention, the beam splitter is implemented as a cube beam splitter or as a pellicle beam splitter.

The normal incidence PSD sensor has a housing which encases the illumination source, the imaging sensor, the optical absorber, and the beam splitter to prevent the interior of normal incidence PSD sensor from contamination, such as dust particles, etc. which might distort the light pattern directed to the surface of the specimen and the light pattern reflected from the surface of the specimen. In one exemplary embodiment, the housing includes a viewing window. The viewing window faces towards the surface of the specimen. In another exemplary embodiment, the viewing window in the housing is omitted and in its place, only a portion of the beam splitter is encased by the housing and a front face of the beam splitter that is directed to the surface of the specimen forms a part of the housing and defines the viewing area.

The normal incidence PSD sensor further includes a mounting system arranged on the housing, which permits the normal incidence PSD sensor to be mounted on a robot arm, a robot mover, a multi-axis stage, or on any type of movable or stationary structure.

According to an aspect of the invention, the illumination source is a liquid-crystal display (LCD) emitting non-coherent light, the imaging sensor is a camera having a resolution of 26 megapixels, the optical absorber is an antireflective neutral density filter, the surface of the specimen is a planar surface, and the imaging optic is a magnification lens having a focal plane at the planar surface of the specimen.

According to another aspect of the invention, the light pattern emitted by the illumination source is a sinusoidal light intensity pattern.

According to yet another aspect of the invention, the illumination source is a light-emitting diode (LED) array.

The object is further achieved by a system for optically inspecting the surface of a specimen with the normal incidence PSD sensor. The system includes the normal incidence PSD sensor and a data processing apparatus in communication with the normal incidence PSD sensor via a communication interface. The normal incidence PSD sensor may be mounted on a robot mover or on a multi-axis stage to permit the normal incidence PSD sensor to be moved relative to the surface of the specimen to be inspected.

The data processing apparatus is configured to: generate the light pattern and at least one phase-shifted light pattern, the at least one phase-shifted light pattern including the first areas in which light is emitted with the first light intensity and the second areas in which the light is emitted with the second light intensity, and corresponding first and second areas in the light pattern and the at least one phase-shifted light pattern being phase-shifted relative to each other, and determine properties of the surface of the specimen based on an evaluation of the at least one sensor image.

The method is further achieved by a method for optically inspecting a surface of a specimen with a normal incidence PSD sensor, the method including: generating a light pattern and at least one phase-shifted light pattern, the light pattern and the at least one phase-shifted light pattern including first areas in which light is emitted with a first light intensity and second areas in which the light is emitted with a second light intensity, the first light intensity being higher than the second light intensity, and corresponding first and second areas in the light pattern and the at least one phase-shifted light pattern being phase-shifted relative to each other, subsequently illuminating the surface of the specimen with the light pattern and the at least one phase-shifted light pattern, capturing the light pattern and the at least one phase-shifted light pattern reflected from the surface of the specimen with an imaging sensor in at least one sensor image at a scanning position, and determining properties of the surface based on an evaluation of the at least one sensor image.

According to another aspect of the invention, the method further includes: defining an inspection cell, moving the specimen into the inspection cell, moving at least one of (a) the normal incidence PSD sensor in the inspection cell relative to the specimen or (b) the specimen in the inspection cell relative to normal incidence PSD sensor to at least one scanning position at which the focal axis of the imaging sensor is aligned to coincide with the normal vector of the surface of the specimen, and capturing the light pattern and the at least one phase-shifted light pattern reflected from the surface of the specimen by the imaging sensor in the at least one sensor image at the at least one scanning position.

BRIEF DESCRIPTION OF THE DRAWINGS

The invention will now be described with reference to the drawings wherein.

DESCRIPTION OF EXEMPLARY EMBODIMENTS

Identical reference signs hereinafter designate elements having identical or similar technical features.

Figure 1:
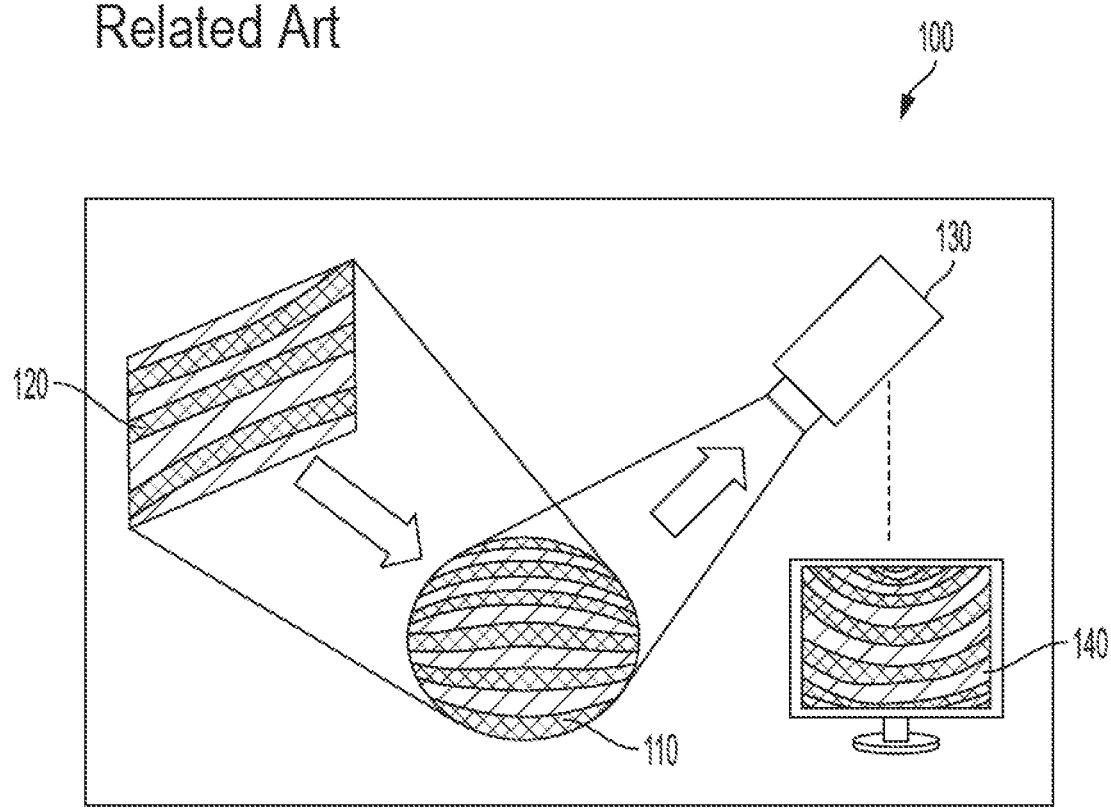
FIG. 1 shows a schematic illustration of a conventional phase-shifted deflectometry setup.
Figure 2:
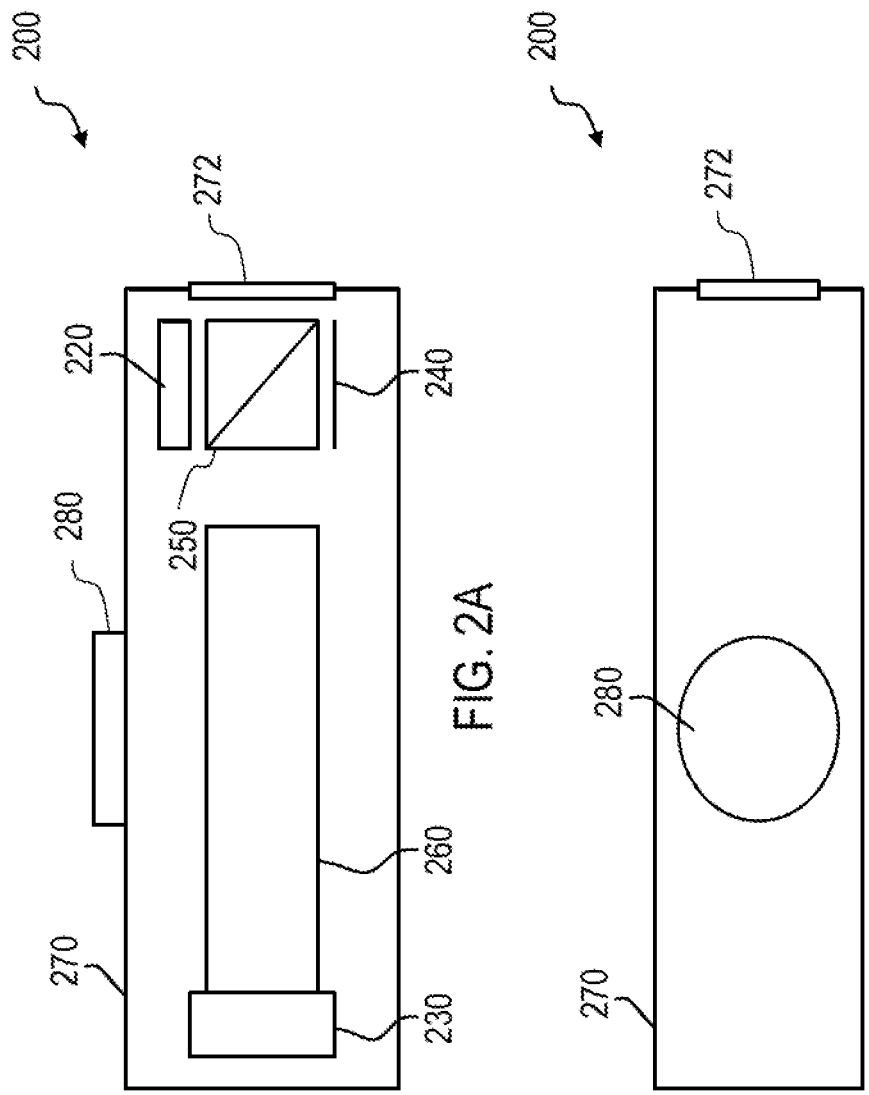
FIG. 2A shows a schematic illustration of a top view of a normal incidence PSD sensor according to a first exemplary embodiment of the invention.
FIG. 2B shows a schematic illustration of a side view of the normal incidence PSD sensor according to the first exemplary embodiment of the invention.

FIG. 2A shows a schematic illustration of a top view of a normal incidence PSD sensor 200 for optically inspecting a surface of a specimen. The normal incidence PSD sensor 200 includes an illumination source 220, an imaging sensor 230, an optical absorber 240, a beam splitter 250, and imaging optic 260.

The normal incidence PSD sensor 200 may have a height and width in a range between 80 millimeters (mm) and 130 mm and a length in a range between 400 mm and 500 mm, and it may be placed at a distance of about 43 mm from the surface to be inspected during normal operation. Such a configuration may diminish defocus and blur effects that may be encountered when operating the normal incidence PSD sensor 200 in a soft-microscopy setup.

As shown in FIG. 2A, the illumination source 220 is arranged on one side of the beam splitter 250 and the optical absorber 240 is arranged on an opposite side of the beam splitter 250. As shown in more detail in FIG. 5 below, the beam splitter 250 directs a portion of the light emitted from the illumination source 220 to the optical absorber and another portion of the light emitted from the illumination source 220 to the surface of the specimen (not shown). In addition, the beam splitter 250 directs the light pattern reflected from the surface of the specimen to the imaging sensor 230, which is captured by the imaging sensor 230 after the light pattern passed through imaging optic 260 arranged between the beam splitter 250 and the imaging sensor 230.

As a result, the beam splitter 250 allows emitting normal incidence light from the illumination source 220 to the surface of the specimen and collecting light reflected from the surface of the specimen in an acquisition without changing the position of the normal incidence PSD sensor 200.

Figure 3:
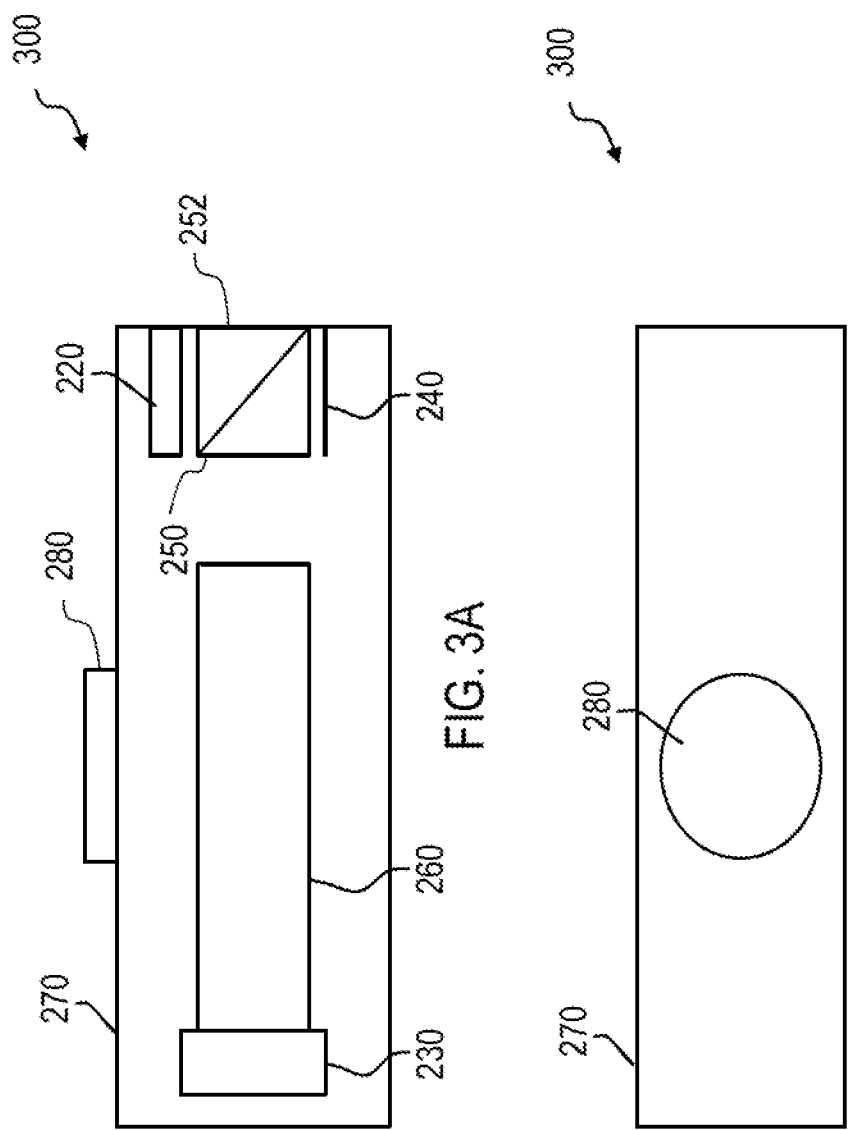
FIG. 3A shows a schematic illustration of a top view of a normal incidence PSD sensor according to a second exemplary embodiment of the invention.
FIG. 3B shows a schematic illustration of a side view of the normal incidence PSD sensor according to the second exemplary embodiment of the invention.
Figure 5:
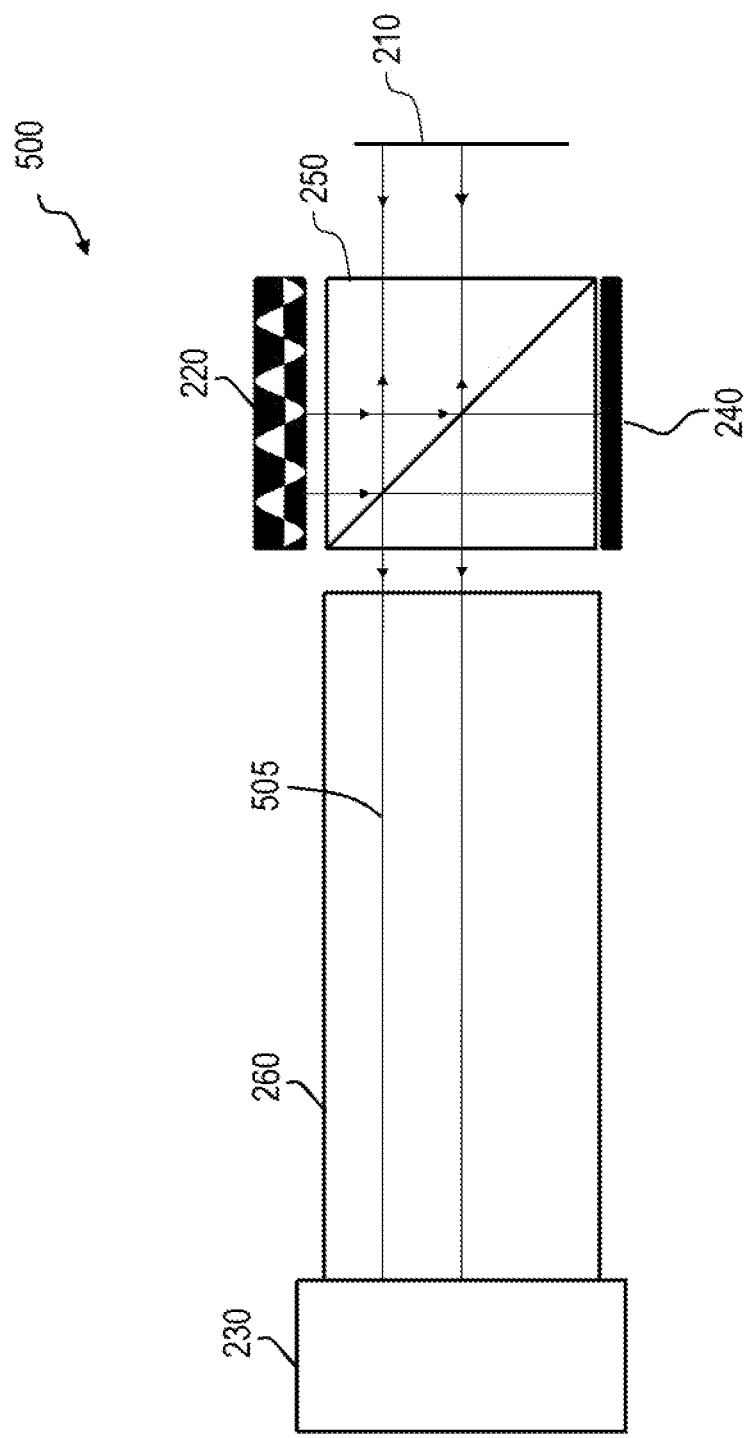
FIG. 5 shows a schematic illustration of a light beam path in a system for inspecting a surface of a specimen with a normal incidence PSD sensor according to an exemplary embodiment of the invention.

The beam splitter may be a cube beam splitter, such as the beam splitter 250 shown in FIGS. 2A, 3A, and 5. Each face of the cube beam splitter may have a dimension of 80 mm×80 mm. However, the dimension of the cube beam splitter is not limited thereto. For example, it is also possible to use a cube beam splitter having a dimension of 1 meter (m)×1 m. Of course, the overall dimensions of the normal incidence PSD sensor are also adjusted accordingly.

Cube beam splitters are typically made of a pair of precision right-angle prisms which are cemented together at their base thereby forming a layer between the right-angle prisms. The thickness of the layer is selected such that half of the light incident through one face of the cube beam splitter is reflected and another half of the light is transmitted through the cube beam splitter as a result of frustrated total internal reflection. Such beams splitters are also called 50/50 beam splitters.

The optical absorber 240 may be an AR ND filter which is provided to quell any light carrying any information that may pollute the light pattern reflected from the surface of the specimen and directed to the imaging sensor. In other words, the optical absorber 240 provides an optical attenuation. It is also possible to utilize a filter with black absorbing diffused layers. The optical absorber 240 absorbs the portion of the light that passes the beam splitter and that is not directed to the surface to be inspected. This portion of the light is absorbed by the optical absorber 240 to prevent specular components of reflection in the normal incidence PSD sensor.

With the normal incidence PSD sensors 200, 300, and 400 shown in FIGS. 2A to 4, inspection on a very fine scale can be provided while using the entire field of view of the imaging sensor 230 that is aligned with normal incidence to the surface to inspect. The imaging sensor 230 may be a camera sensor, e.g., a charge-coupled device (CCD) sensor or a complementary metal-oxide-semiconductor (CMOS) sensor, having a resolution of 26 megapixels. However, the imaging sensor is not limited thereto. Higher or lower resolutions are also possible. The imaging optic 260 may be, but is not limited to, a 1.33× magnification lens creating an object pixel size of 3.5 micron and a field of view of approximately 15×15 mm.

The illumination source 220 may be an LCD display emitting non-coherent light. According to an exemplary embodiment of the invention, the acquisition time is approximately one second for a full set of 5 sensor images to reconstruct surface slopes in two orthogonal directions. Other acquisition times are also possible. Image acquisition time on glass surfaces may be limited by the light output of the LCD display.

According to an aspect of the invention, it is possible to use deflectometry with very dense fringes and Fourier transformation to extract phase information. In this case, only one sensor image is needed per acquisition to determine gloss level and form of the surface of the specimen.

According to another exemplary embodiment of the invention, the illumination source 220 is implemented as an LED array which improves the light output performance. When the LED array is utilized, performance of the normal incidence PSD sensors 200, 300, and 400 may be limited by the data acquisition rate of the imaging sensor 230 and an acquisition speed of approximately 160 milliseconds (ms) for all 5 images may be obtained. The sensitivity to defects with lateral dimensions may be in the order of 10 micrometers (μm) and depths of 6 nanometers (nm) on both glass and silicon surfaces. Thus, it is this combination of depth sensitivity over a rather large dynamic range combined with the speed of data acquisition that is of particular importance for this sensor geometry.

It is also possible to measure a surface height on a 3D structure with white light interferometry (WLI). Surface profiles inspected with WLI may vary between tens of nanometers and a few centimeters. When compared with white light interferometry (WLI), the normal incidence PSD sensors 200, 300, and 400 shown in FIGS. 2A to 4 exhibits some key advantages.

Contrary to the normal incidence PSD sensors 200, 300, and 400, the WLI technology requires a scanning reference mirror with high reflectance which is moved relative to an illumination unit. WLI technology utilizes coherent light, whereas the illumination source of the normal incidence PSD sensors 200, 300, and 400 emit non-coherent light.

A WLI interferometer captures interference pattern created by addition of light collected from the interference between the light reflected from the target and from a reference mirror and the intensity of the light emitted from the illumination unit does not change. To the contrary, there is no reference pattern utilized with the normal incidence PSD sensors 200, 300, and 400. The light emitted by illumination source 220 is non-coherent light and the illumination pattern shifts between each data point per one region of interest.

Although WLI has been demonstrated to exhibit an acceptable depth sensitivity, the depth sensitivity comes at the cost of a slow scan speed. In addition, white light interferometers are designed to solely capture the depth information on a surface, while the normal incidence PSD sensors 200, 300, and 400 shown in FIGS. 2A to 4 also capture information related to the gloss level. However, the gloss level inspection is key to detecting specific defect types, predominately contamination on optical surfaces where there is no significant change in surface height. Lastly, WLI requires fine motion control of the reference arm of the interferometer. In the case of the normal incidence PSD sensors 200, 300, and 400 shown in FIGS. 2A to 4, there is no mechanical manipulation of any element of the normal incidence PSD sensors required, making the data acquisition much simpler.

The normal PSD sensor 200 further includes a housing 270 and a mounting system 280 arranged on the housing 270. The housing 270 of the normal PSD sensor 200 in the exemplary embodiment shown in FIGS. 2A and 2B has a viewing window 272 facing towards the surface of a specimen (not shown). The housing prevents the interior of normal incidence PSD sensor 200 from contamination, such as dust particles, etc., which might distort the light pattern directed to the surface of the specimen and the light pattern reflected from the surface of the specimen.

The beam splitter 250 of the normal PSD sensor 300 shown in FIG. 3A includes a front face 252 which forms a part of the housing 270. Thereby, a viewing window such as the viewing window 272 shown in FIG. 2A can be dispensed of.

Figure 4:
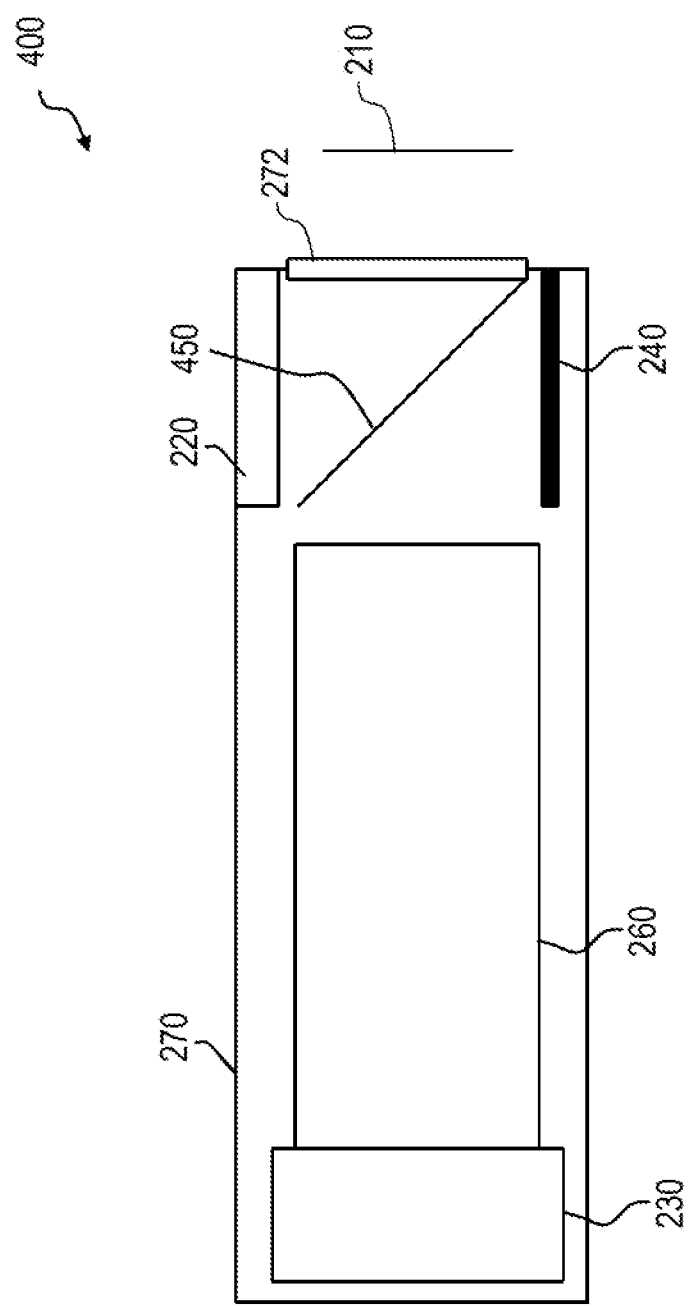
FIG. 4 shows a schematic illustration of a top view of a normal incidence PSD sensor according to a third exemplary embodiment of the invention.

FIG. 4 shows a schematic illustration of a top view of a normal incidence PSD sensor 400 according to a third exemplary embodiment of the invention, similar to the exemplary embodiment shown in FIG. 2A. However, the normal incidence PSD sensor 400 shown in FIG. 4 includes a pellicle beam splitter 450.

Pellicle beam splitters or pellicle mirrors are very thin semi-transparent membranes typically made of lightweight polymer. Such beam splitters are also called plate beam splitters. These membranes may be stretched and bonded over a flat aluminum frame. Due to the thinness of the membrane, images from secondary reflections are eliminated and the light beam is split into two separate beams, both of reduced light intensity.

Contrary to the cube beam splitter shown in FIG. 3A, the pellicle beam splitter 450 cannot seal the housing 270. Therefore, the normal incidence PSD sensor 400 according to the third exemplary embodiment shown in FIG. 4 includes the viewing window 272.

FIG. 5 shows a schematic illustration of a light beam path 505 in a system 500 for inspecting a surface of a specimen with a normal incidence PSD sensor according to an exemplary embodiment of the invention. As shown in FIG. 5, a light pattern is emitted from the illumination source 220. The light pattern may be a sinusoidal light intensity pattern, as illustrated in FIG. 5. However, any other light pattern is also possible, as long as it allows to determine phase shifts and changes in the light intensities of in the pattern reflected from the surface 210 of the specimen to be inspected.

The beam splitter 250 in the system 500 for optical surface inspection is a 50/50 cube beam splitter. As shown in FIG. 5, a portion of the light emitted from the illumination source 220 is reflected on the layer between the two right-angle prisms and directed to the surface 210 of the specimen. The other half of the light emitted from the illumination source 220 is transmitted through the cube beam splitter 250 as a result of frustrated total internal reflection toward the optical absorber 240.

The light pattern reflected from the surface 210 of the specimen passes entirely through the beam splitter 250 and the imaging optic 260 to the imaging sensor 230.

Figure 6:
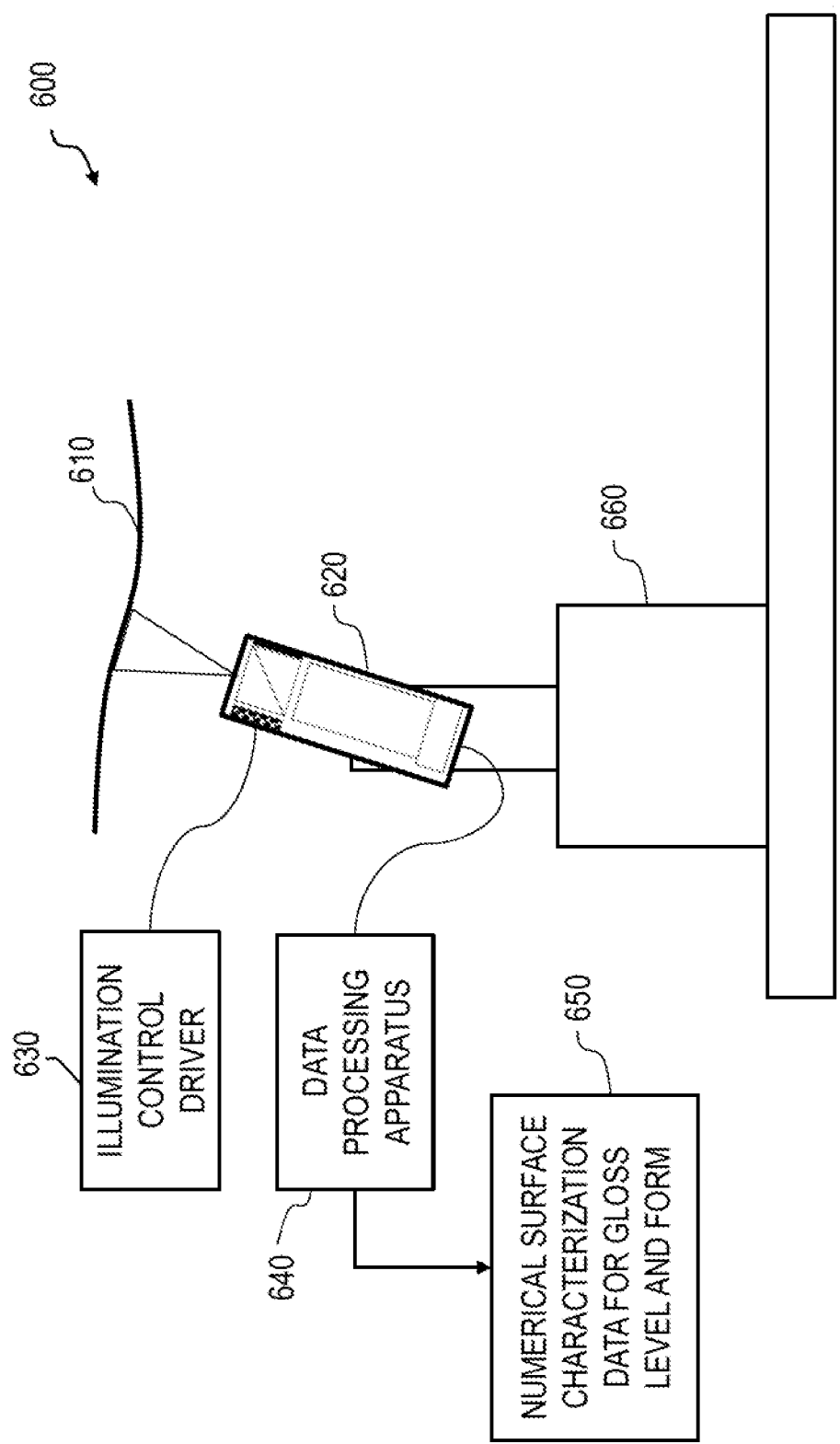
FIG. 6 shows a schematic illustration of a system for inspecting a surface of a specimen with a normal incidence PSD sensor according to an exemplary embodiment of the invention.

FIG. 6 shows a schematic illustration of a system 600 for inspecting a surface 610 of a specimen with a normal incidence PSD sensor 620. The system 600 includes an illumination control driver 630 in communication with the illumination source of the normal incidence PSD sensor 620. The system further includes a data processing apparatus 640 in communication with the imaging sensor of the normal incidence PSD sensor 620. As shown in FIG. 6, the data processing apparatus 640 outputs numerical data 650 characterizing the gloss level and the form of the surface 610 of the specimen.

The normal incidence PSD sensor 620 of the system 600 for inspecting the surface 610 of the specimen is mounted on a robot mover 660. Instead of a robot mover 660, the normal incidence PSD sensor 620 may also be mounted on a multi-axis stage.

As shown in FIG. 6, the surface 610 of the specimen may not be entirely planar. Based on the reflected light pattern, the data processing apparatus 640 may detect the position of the normal incidence PSD sensor 620 relative to the surface 610. The data processing apparatus 640 may send the position data via network interface 740 and network 770 shown in FIG. 7 to the robot mover 660 to adjust the position of the normal incidence PSD sensor 620 and to keep the normal incidence PSD sensor 620 in a normal incidence position relative to the portion of the surface 610 of the specimen under inspection.

Upon completion of the determination of the properties of the surface 610 by the data processing apparatus 640 based on an evaluation of at least one sensor image, the data processing apparatus 640 outputs numerical surface characterization data for gloss level and form of the surface 610.

Figure 7:
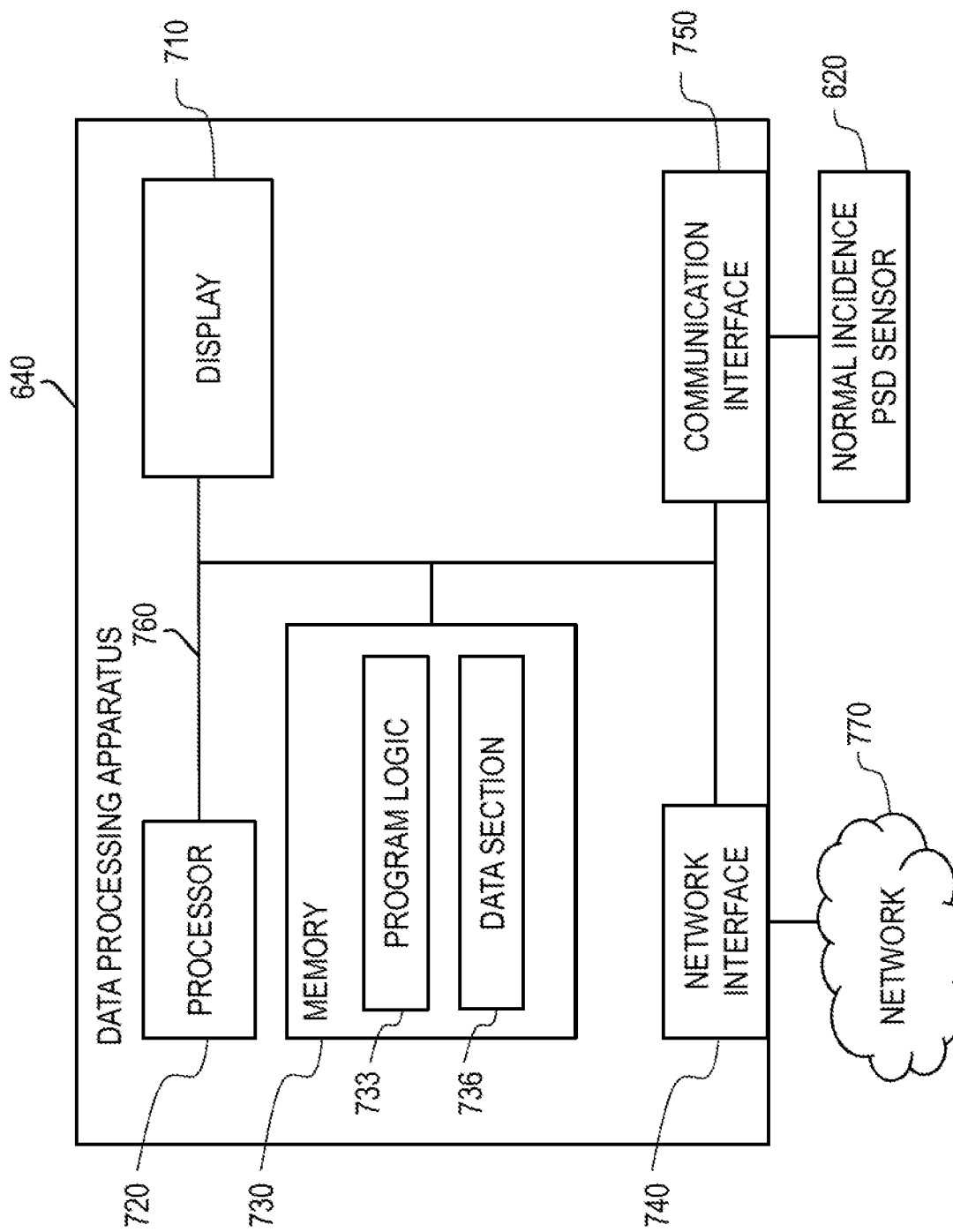
FIG. 7 shows a schematic illustration of a data processing apparatus according to an exemplary embodiment of the invention.

FIG. 7 shows a schematic illustration of a data processing apparatus 700. Data processing apparatus 700 may be implemented by any conventional or other computer system optionally equipped with a display or monitor 710, at least one processor 720, at least one memory 730 and/or at least one internal or external network interface 740 (e.g., modem, network cards, etc.) and at least one communication interface 750, optional an input device (e.g., a keyboard, mouse, or other input device), and any commercially available or custom software. Display or monitor 710, the at least one processor 720, the at least one memory 730, the at least one internal or external network interface 740, and the at least one communication interface 750 are connected with each other via a data bus 760.

Memory 730 includes a program logic module 733, which is configured to store a program logic, and a data section module 736, which is configured to store data, e.g., image data and numerical surface characterization data 650, e.g., for gloss level and form or shape of the surface 610 of the specimen. Communication interface 750 is configured to communicate with the normal incidence PSD sensor 620 via a communication link to receive the sensor image captured by the normal incidence PSD sensor. The sensor image is stored in the data section module 736 in the memory 730.

Program logic module 733 includes a program logic that contains instructions executed by the at least one processor 3720. The memory 730 includes a computer readable storage medium that may be non-transitory, and, may be, but is not limited to, an electronic storage device, a magnetic storage device, an optical storage device, an electromagnetic storage device, a semiconductor storage device, or any suitable combination of the foregoing, including a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), and a memory stick.

The program logic includes further instructions to determine properties of the surface including numerical surface characterizations of gloss level and form. The properties are determined based on intensity, phase, and amplitude (intensity, phase, and amplitude channels). The amplitude channel carries information about changes in gloss on the surface. The phase is directly comparable to the slope of the surface of the object.

The processor 720 provides numerical surface characterization data 650, e.g., for gloss level and form of the surface, that can be displayed on a display 710 or that can be forwarded through network interface 740 and network 770 to a main production control system (not shown), etc.

Figure 8:
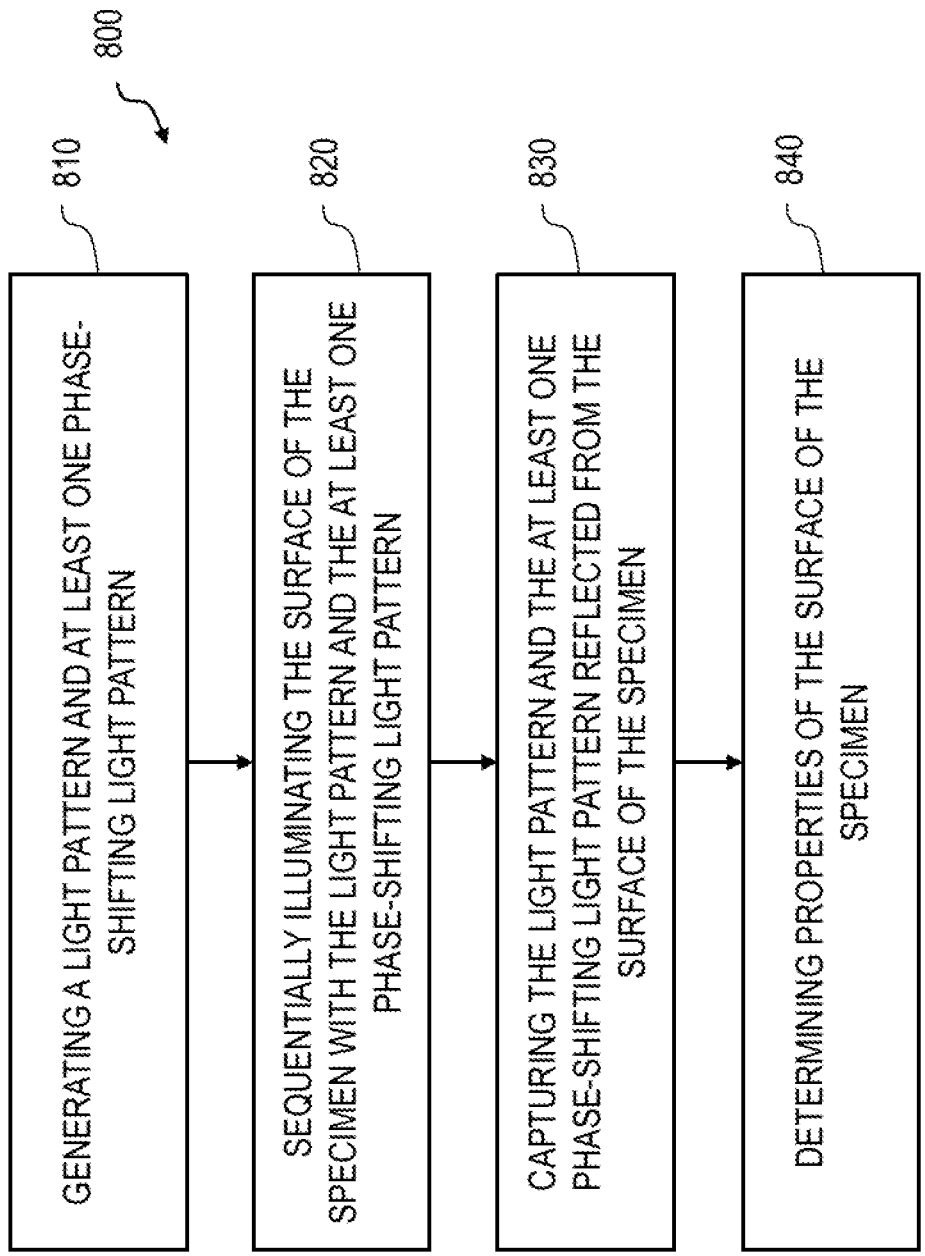
FIG. 8 shows a flow chart of a method for inspecting a surface of a specimen with a normal incidence PSD sensor according to an exemplary embodiment of the invention.

FIG. 8 shows an illustration of a method 800 for inspecting a surface 610 of a specimen according to an exemplary embodiment of the invention. The method begins with step 810 in which a light pattern and at least one phase-shifting light pattern are generated, e.g., by illumination control driver 630 shown in FIG. 6. The light pattern includes first areas in which light is emitted with a first light intensity and second areas in which light is emitted with a second light intensity. In step 820, the surface 610 of the specimen is sequentially illuminated with the light pattern and the at least one phase-shifting light pattern emitted by the illumination source 220. In step 830, the light pattern and the at least one phase-shifting light pattern reflected from the surface of the specimen are captured by the imaging sensor 230. Once the light pattern and the at least one phase-shifting light pattern reflected from the surface of the specimen are captured, the method 800 proceeds to step 840 in which properties of the surface 610 of the specimen are determined by the data processing apparatus 700.

Figure 9:
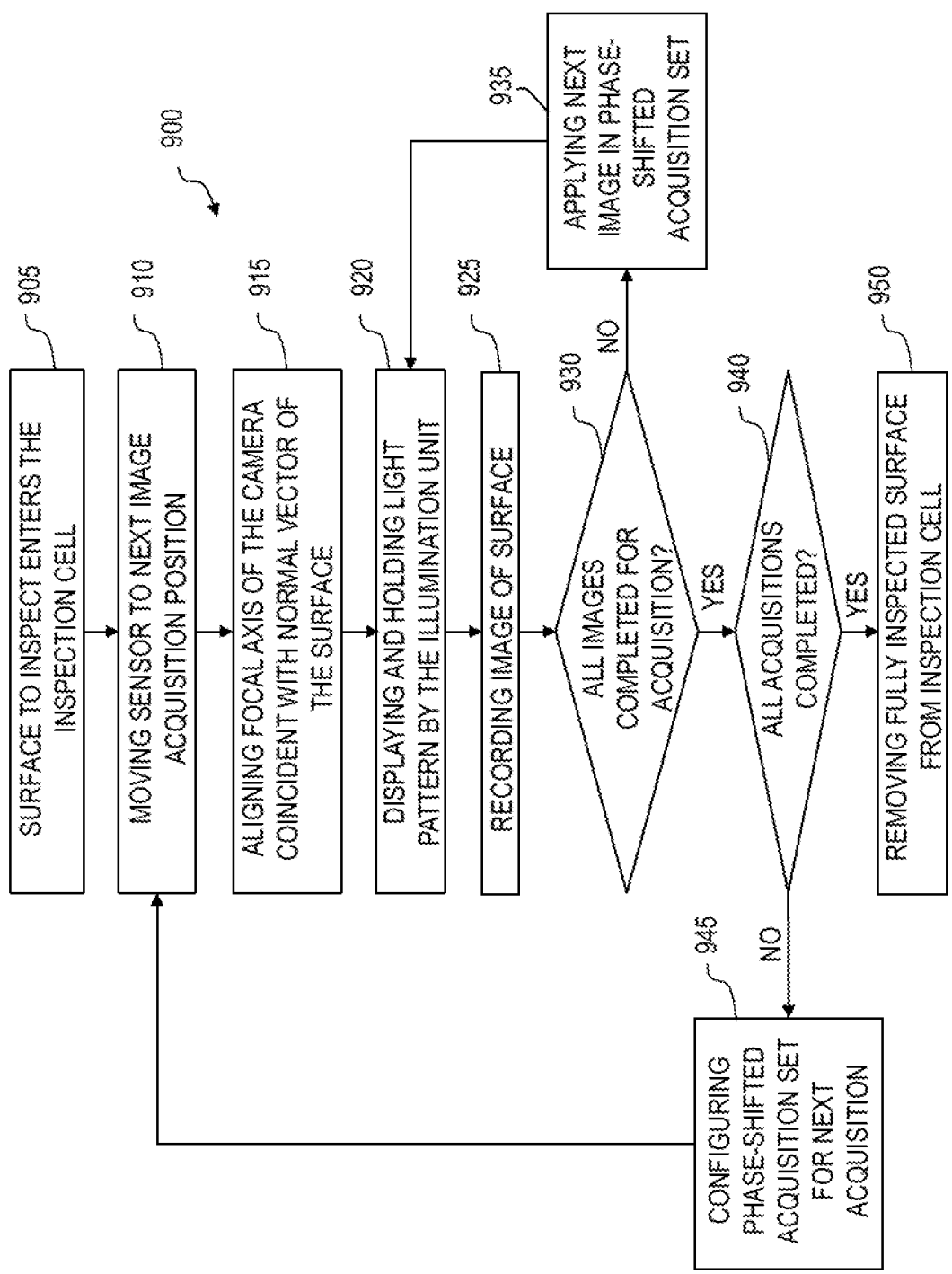
FIG. 9 shows a flow chart of a method for inspecting a surface of a specimen with a normal incidence PSD sensor according to another exemplary embodiment of the invention.

FIG. 9 is a detailed illustration of a method 900 for inspecting a surface 610 of a specimen in an inspection cell. Method 900 begins with step 905 in which the surface 610 of the specimen to be inspected enters an inspection cell. In step 910, once the specimen is in the inspection cell, the normal incidence PSD sensor 620 moves to an image acquisition position. It is also possible that both, the normal incidence PSD sensor 620 and the surface 610 of the specimen to be inspected are moving relative to one another or that only the surface of the specimen moves to the image acquisition position and the normal incidence PSD sensor 620 is fixedly installed in a stationary position. In step 915 at the image acquisition position, the focal axis of the imaging sensor 230 of the normal incidence PSD sensor 620 is aligned to coincide with the normal vector of the surface 610 of the specimen to be inspected. In step 920, the illumination source 220 of the normal incidence PSD sensor 620 displays and holds a light pattern and in step 925, the imaging sensor 230 of the normal incidence PSD sensor 620 captures and records at least one sensor image of the light pattern reflected from the surface 610 of the specimen.

The method 900 then moves to step 930 in which the data processing apparatus 640 determines whether all sensor images are taken for the respective acquisition at the respective acquisition position. Upon determining that not all sensor images are taken for the respective acquisition at the respective acquisition position, the method 900 moves to step 935 at which the next image in the phase-shifted acquisition set is applied and the method 900 returns to step 920. Upon determining that all sensor images are taken for the respective acquisition at the respective acquisition position in step 930, the method moves to step 940 in which it is determined whether all acquisitions of the surface 610 of the specimen to be inspected are completed.

If it is determined in step 940 that all acquisitions of the surface 610 of the specimen to be inspected are completed, the method 900 moves to step 950 in which the fully inspected surface 610 is removed from the inspection cell.

If it is determined in step 940 that not all acquisitions of the surface 610 of the specimen to be inspected are completed, the method 900 moves to step 945 in which the phase-shifted acquisition set for the next acquisition is configured. Subsequent to step 945, the method 900 returns to step 910.

In summary, the new normal incidence PSD sensor technique enables imaging at normal incidence, which is a key enabler in the imaging of fine defects on optical surfaces. This technique permits obtaining resolutions with a PSD sensor below that of macro photography and brings the PSD technology into the realm of soft-microscopy. Imaging at normal incidence alleviates the key limitation of PSD, i.e., the defocus across the field of view of the sensor. The normal incidence PSD sensors 200, 300, and 400 have demonstrated applicability in the inspection of ultra-high polished optical surfaces with an exceptional speed of data acquisition and no mechanical scanning requirement.

The term "comprising" (and its grammatical variations) as used herein is used in the inclusive meaning of "having" or "including" and not in the exclusive sense of "consisting only of." The terms "a" and "the" as used herein are understood to encompass the plural as well as the singular.

It is understood that the foregoing description is that of the exemplary embodiments of the invention and that various changes and modifications may be made thereto without departing from the spirit and scope of the invention as defined in the appended claims.

What is claimed is:

1. A normal incidence phase-shifted deflectometry (PSD) sensor for optically inspecting a surface of a specimen, the sensor comprising:
   an illumination source configured to illuminate the specimen with a light pattern, the light pattern including first areas in which light is emitted with a first light intensity and second areas in which the light is emitted with a second light intensity, the first light intensity being higher than the second light intensity, the illumination source being arranged relative to the surface of the specimen to permit the illumination source to emit the light perpendicular to the surface of the specimen;

an imaging sensor configured to capture the light pattern reflected from the surface of the specimen in a sensor image;

an optical absorber configured to absorb a first portion of the light emitted from the illumination source;

a beam splitter arranged between the illumination source and the optical absorber and configured to direct (a) the first portion of the light from the illumination source to the optical absorber, (b) a second portion of the light from the illumination source to the surface of the specimen, and (c) the light pattern reflected from the surface of the specimen to the imaging sensor; and an imaging optic arranged between the imaging sensor and the beam splitter.

2. The normal incidence PSD sensor of claim 1, wherein the beam splitter is a cube beam splitter.

3. The normal incidence PSD sensor of claim 2, further comprising:
a housing encasing the illumination source, the imaging sensor, the optical absorber, and a portion of the beam splitter; and
a mounting system arranged on the housing,
wherein the beam splitter includes a front face directed to the surface of the specimen and forming a part of the housing.

4. The normal incidence PSD sensor of claim 1, wherein the beam splitter is a pellicle beam splitter.

5. The normal incidence PSD sensor of claim 1, further comprising:
a housing including a viewing window facing towards the surface of the specimen, the housing encasing the illumination source, the imaging sensor, the optical absorber, and the beam splitter; and
a mounting system arranged on the housing.

6. The normal incidence PSD sensor of claim 1, wherein:
the illumination source is a liquid-crystal display (LCD) emitting non-coherent light,
the imaging sensor is a camera having a resolution of 26 megapixels,
the optical absorber is an antireflective neutral density filter,
the surface of the specimen is a planar surface, and
the imaging optic is a magnification lens having a focal plane on the planar surface of the specimen.

7. The normal incidence PSD sensor of claim 1, wherein the light pattern is a sinusoidal light intensity pattern.

8. The normal incidence PSD sensor of claim 1, wherein the illumination source is a light-emitting diode (LED) array.

9. A system for optically inspecting a surface of a specimen with a normal incidence PSD sensor, the system comprising:
a normal incidence PSD sensor including:
an illumination source configured to illuminate the specimen with a light pattern, the light pattern including first areas in which light is emitted with a first light intensity and second areas in which the light is emitted with a second light intensity, the first light intensity being higher than the second light intensity, and the illumination source being arranged relative to the surface of the specimen to permit the illumination source to emit the light perpendicular to the surface of the specimen;

an imaging sensor configured to capture the light pattern reflected from the surface of the specimen in at least one sensor image;

an optical absorber configured to absorb a first portion of the light emitted from the illumination source;

a beam splitter arranged at a predefined distance from the surface of the specimen, the illumination source being arranged on a first side of the beam splitter, the optical absorber being arranged on a second side of the beam splitter opposite to the first side, and the beam splitter being configured to direct (a) the first portion of the light from the illumination source to the optical absorber, (b) a second portion of the light from the illumination source to the surface of the specimen, and (c) the light pattern reflected from the surface of the specimen to the imaging sensor; and an imaging optic arranged between the imaging sensor and the beam splitter; and a data processing apparatus in communication with the normal incidence PSD sensor via a communication interface.

10. The system of claim 9, wherein the data processing apparatus is configured to:
generate the light pattern and at least one phase-shifted light pattern, the at least one phase-shifted light pattern including the first areas in which light is emitted with the first light intensity and the second areas in which the light is emitted with the second light intensity, and corresponding first and second areas in the light pattern and the at least one phase-shifted light pattern being phase-shifted relative to each other; and
determine properties of the surface of the specimen based on an evaluation of the at least one sensor image.

11. The system of claim 9, wherein the beam splitter is a cube beam splitter.

12. The system of claim 11, wherein:
the normal incidence PSD sensor further includes a housing and a mounting system,
the housing encases the illumination source, the imaging sensor, the optical absorber, and a portion of the beam splitter,
the mounting system is arranged on the housing, and
the beam splitter includes a front face directed to the surface of the specimen and forming a part of the housing.

13. The system of claim 9, wherein the beam splitter is a pellicle beam splitter.

14. The system of claim 13, wherein the normal incidence PSD sensor further includes a housing having a viewing window facing towards the surface of the specimen, the housing encasing the illumination source, the imaging sensor, the optical absorber, and the beam splitter, and wherein a mounting system is arranged on the housing.

15. The system of claim 9, wherein:
the illumination source is a liquid-crystal display (LCD) emitting non-coherent light,
the imaging sensor is a camera,
the optical absorber is an antireflective neutral density filter,
the surface of the specimen is a planar surface and
the imaging optic is a magnification lens having a focal plane on the planar surface of the specimen.

16. The system of claim 9, wherein the light pattern is a sinusoidal light intensity pattern.

17. The system of claim 9, wherein the illumination source is a light-emitting diode (LED) array.

18. The system of claim 9, further comprising at least one of a robot mover or a multi-axis stage, and the normal incidence PSD sensor being mounted on the at least one of the robot mover or the multi-axis stage.

19. A method for optically inspecting a surface of a specimen with a normal incidence phase-shifted deflectometry (PSD) sensor, the method comprising:

generating a light pattern and at least one phase-shifted light pattern, the light pattern and the at least one phase-shifted light pattern including first areas in which light is emitted with a first light intensity and second areas in which the light is emitted with a second light intensity, the first light intensity being higher than the second light intensity, and corresponding first and second areas in the light pattern and the at least one phase-shifted light pattern being phase-shifted relative to each other;

subsequently illuminating the surface of the specimen with the light pattern and the at least one phase-shifted light pattern;

capturing the light pattern and the at least one phase-shifted light pattern reflected from the surface of the specimen with an imaging sensor in at least one sensor image at a scanning position, the imaging sensor defining a focal axis and the surface of the specimen defining a normal vector;

determining properties of the surface based on an evaluation of the at least one sensor image;

defining an inspection cell;

moving the specimen into the inspection cell;

moving at least one of (a) the normal incidence PSD sensor in the inspection cell relative to the specimen or (b) the specimen in the inspection cell relative to normal incidence PSD sensor to at least one scanning position at which the focal axis of the imaging sensor is aligned to coincide with the normal vector of the surface of the specimen; and capturing the light pattern and the at least one phase-shifted light pattern reflected from the surface of the specimen by the imaging sensor in the at least one sensor image at the at least one scanning position.

20. The method of claim 19, wherein the light pattern and the at least one phase-shifted light pattern are sinusoidal light intensity patterns.

* * * * *